(12) United States Patent
Jaehne et al.

(10) Patent No.: US 6,686,397 B2
(45) Date of Patent: Feb. 3, 2004

(54) POLYSUBSTITUTED INDAN-1-OL SYSTEMS FOR THE PROPHYLAXIS OR TREATMENT OF OBESITY

(75) Inventors: Gerhard Jaehne, Frankfurt (DE); Volker Krone, Hofheim (DE); Martin Bickel, Bad Homburg (DE); Matthias Gossel, Hofheim (DE)

(73) Assignee: Aventis Pharma Deutschland GmbH (DE)

( * ) Notice: Subject to any disclaimer, the term of this patent is extended or adjusted under 35 U.S.C. 154(b) by 0 days.

(21) Appl. No.: 10/230,353

(22) Filed: Aug. 29, 2002

(65) Prior Publication Data

US 2003/0130323 A1 Jul. 10, 2003

(30) Foreign Application Priority Data

Aug. 31, 2001 (DE) .......................... 101 42 659

(51) Int. Cl.[7] .......................... A61K 31/10; A61K 31/19
(52) U.S. Cl. .................. 514/709; 514/706; 514/602; 568/34; 564/340; 562/41; 562/405
(58) Field of Search ............... 568/28, 30, 31, 568/32, 33, 34; 564/305, 340; 562/30, 41, 400, 405; 514/601, 602, 706, 709

(56) References Cited

U.S. PATENT DOCUMENTS

| | | | |
|---|---|---|---|
| 4,244,960 A | * | 1/1981 | Schroder et al. ............ 514/351 |
| 4,375,479 A | * | 3/1983 | Schroeder et al. .......... 514/605 |

FOREIGN PATENT DOCUMENTS

| | | |
|---|---|---|
| DE | 2 345 146 | 3/1976 |
| WO | WO 97 20806 A | 6/1997 |
| WO | WO 97/20806 | 6/1997 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 01/12176 | 2/2001 |
| WO | WO 01 62746 A1 | 8/2001 |
| WO | WO 01 02373 A | 1/2002 |

OTHER PUBLICATIONS

CA:121:9577 abs of Journal of Organometallic Chemistry by Cambie et al 467(2) pp 237–244 1994.*

Lambert, P.D., et al., "Ciliary neurotrophic factor activates leptin–like pathways and reduces body fat, without cachexia or rebound weight gain, even in leptin–resistant obesity." *PNAS*, vol. 98, No. 8, Apr. 10, 2001, pp. 4652–4657.

Tyle, P., "Iontophoretic Devices for Drug Delivery." *Pharmaceutical Research*, vol. 3, No. 6, 1986, pp. 318–326.

Venier, Clifford G., et al., "Peroxytrifluoroacetic Acid. A Convenient Reagent for the Preparation of Sulfoxides and Sulfones." *J. Org. Chem.*, vol. 47, 1982, pp. 3773–3774.

Seebach, Dieter, et al., "Herstellung α–thiolierter Carbonylverbindungen." *Chem. Ber.*, vol. 109, 1976, pp. 1601–1616.

A. V. Sviridova et al., A Method for the Selective Oxidation . . . , Translated from *Zhurnal Organicheskoi Khimii,*, vol. 7, No. 12, pp. 2480–2483, Dec., 1971, original Article submitted Dec. 21, 1970 (translated pages include 2577–2580).

D. Edwards et al., "The Oxidation of Alkyl Sulphides". *J. Chemical Society*, 1954, pp. 3272–3284.

Hugh W. Thompson., "Sterochemical Control of Reductions. The Directive Effect of Carbomethoxy vs. Hydroxymethyl Groups in Catalytic Hydrogenation" *The Journal of Organic Chemistry* 1971, pp. 2577–2581.

* cited by examiner

*Primary Examiner*—Jean F. Vollano
(74) *Attorney, Agent, or Firm*—Heller Ehrman White and McAuliffe

(57) ABSTRACT

Polysubstituted indan-1-ol compounds of formula I, its physiologically acceptable salts and physiologically functional derivatives are disclosed:

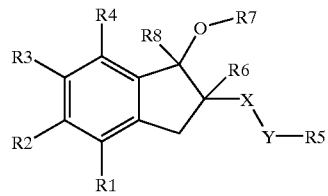

Compositions comprising the same, methods of preparation and methods for the prophylaxis or treatment of obesity are also disclosed herein.

10 Claims, No Drawings

POLYSUBSTITUTED INDAN-1-OL SYSTEMS FOR THE PROPHYLAXIS OR TREATMENT OF OBESITY

RELATED APPLICATION DATA

The instant application takes priority from DE 10142659.3 filed Aug. 31, 2001 which is incorporated herein by reference in its entirety.

BACKGROUND OF THE INVENTION

1. Field of the Invention

The invention relates to polysubstituted indan-1-ol compounds and their physiologically acceptable salts and physiologically functional derivatives for the prophylaxis or treatment of obesity.

2. Description of the Related Art

WO 97/20806 discloses cyclopentyl-substituted indan-1-ol derivatives as antiinflammatory substances.

SUMMARY OF THE INVENTION

In a preferred embodiment, the invention provides compounds which can be used for reducing weight in mammals and which are suitable for preventing and treating obesity. The instant compounds s have a therapeutically utilizable anorectic action.

In another preferred embodiment, the invention also provides a pharmaceutical composition comprising an effective amount of a compound of formula I. The pharmaceutical composition may also comprise one or more active compounds suitable for reducing weight or for the treatment of obesity. The instant composition may also comprise one or more compounds suitable for treatment of other disorders.

In another preferred embodiment, the instant invention provides a method for the treating obesity, comprising administering to a subject in need thereof, an effective amount of a compound according to formula.

In another preferred embodiment, the instant invention provides a method of reducing weight in a mammal, comprising administering to said mammal an effective amount of a compound of formula I.

Additional objects, features and advantages of the invention will be set forth in the description which follows, and in part will be obvious from the description, or may be learned by practice of the invention. The objects, features and advantages of the invention may be realized and obtained by means of the instrumentalities and combinations particularly pointed out in the appended claims.

DESCRIPTION OF THE PREFERRED EMBODIMENTS

The invention relates to compounds of the formula (I)

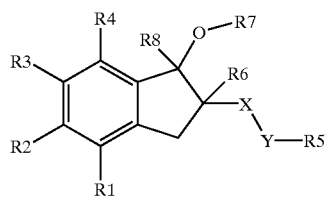

I in which

R1, R2, R3, R4 independently of one another are H, F, Cl, Br, I, CN, $N_3$, $NO_2$, OH, $O(C_1-C_8)$-alkyl, $O(C_3-C_8)$-cycloalkyl, $O-CH_2$-phenyl, O-phenyl, $O-CO-(C_1-C_8)$-alkyl, $O-CO-(C_3-C_8)$-cycloalkyl, where in the alkyl radicals up to seven hydrogen atoms may be replaced by fluorine;

$S(O)_{0-2}(C_1-C_8)$-alkyl, $S(O)_{0-2}(C_3-C_8)$-cycloalkyl, where in the alkyl radicals up to seven hydrogen atoms may be replaced by fluorine; $NH_2$, $NH-(C_1-C_8)$-alkyl, $NH-(C_3-C_8)$-cycloalkyl, $N[(C_1-C_8)$-alkyl$]_2$, $N[(C_3-C_8)$-cycloalkyl$]_2$, $NH-CO-(C_1-C_8)$-alkyl, $NH-CO-(C_3-C_8)$-cycloalkyl;

$SO_3H$; $SO_2-NH_2$, $SO_2-NH-(C_1-C_8)$-alkyl, $SO_2-NH-(C_3-C_8)$-cycloalkyl; $SO_2-(C_1-C_6)$-alkyl; $NH-SO_2-NH_2$; $NH-SO_2-(C_1-C_8)$-alkyl, $NH-SO_2-(C_3-C_8)$-cycloalkyl; $O-CH_2-COOH$, $O-CH_2-CO-O(C_1-C_8)$-alkyl, COOH, COO $(C_1-C_8)$-alkyl, $CO-O-(C_3-C_8)$-cycloalkyl, $CO-NH_2$, $CO-NH(C_1-C_8)$-alkyl, $CO-N[(C_1-C_8)$-alkyl$]_2$;

$(C_1-C_8)$-alkyl, $(C_3-C_8)$cycloalkyl, $(C_2-C_8)$-alkenyl, $(C_2-C_8)$-alkynyl, where in the alkyl, alkenyl and alkynyl groups one to seven hydrogen atoms may be replaced by fluorine;

or one hydrogen may be replaced by OH, $OC(O)CH_3$, $O-CH_2-Ph$, $NH_2$, $NH-CO-CH_3$ or $N(COOCH_2Ph)_2$;

phenyl, 1- or 2-naphthyl,
5-tetrazolyl, 1-$[(C_1-C_6)$-alkyl$]$-5-tetrazolyl, 2-$[(C_1-C_6)$-alkyl$]$-5-tetrazolyl,
1-imidazolyl,
1- or 4-$[1,2,4]$-triazolyl,
2- or 3-thienyl,
2- or 3-furyl,
2-, 3- or 4-pyridyl,
2-, 4- or 5-oxazolyl,
3-, 4- or 5-isoxazolyl,
2-, 4- or 5-thiazolyl,
3-, 4- or 5-isothiazolyl, where the aryl radical or heterocycle may be substituted up to two times by F, Cl, Br, CN,
OH, $(C_1-C_4)$-alkyl, $CF_3$, $O-(C_1-C_4)$-alkyl,
$S(O)_{0-2}(C_1-C_6)$-alkyl, $NH_2$, $NH-SO_2-(C_1-C_4)$-alkyl;
COOH, $CO-O-(C_1-C_4)$-alkyl, $CO-NH_2$ and where in the alkyl groups one to seven hydrogen atoms may be replaced by fluorine; or R2 and R3 together form the radical $-O-CH_2-O-$;

X is S, SO, $SO_2$;

Y is $(CH_2)_p$, where p may be 0, 1, 2 or 3;

R5 is $(C_1-C_{18})$-alkyl, $(C_3-C_8)$-cycloalkyl,
where in the alkyl groups up to seven hydrogen atoms may be replaced by fluorine;
$(CH_2)_{1-6}-COOH$, $(CH_2)_{1-6}-COO-(C_1-C_6)$-alkyl, $(CH_2)_{1-6}-CONH_2$;
$CH_2-CH(NHR10)-COR11$, where R10 may be H or $C(O)-(C_1-C_6)$-alkyl and R11 may be OH, $O-(C_1-C_6)$-alkyl or $NH_2$;
phenyl, 1- or 2-naphthyl, biphenyl or a heterocyclic radical, where the rings or ring systems are in each case substituted up to three times by
F, Cl, Br, I, CN, OH, $O(C_1-C_8)$-alkyl, $O(C_3-C_8)$-cycloalkyl, $O-CO-(C_1-C_8)$-alkyl, $O-CO-(C_3-C_8)$-cycloalkyl, $S(O)_{0-2}(C_1-C_8)$-alkyl, $S(O)_{0-2}(C_3-C_8)$-cycloalkyl, $NH_2$, $NH-(C_1-C_8)$-alkyl, $NH-(C_3-C_8)$-cycloalkyl, $N[(C_1-C_8)$-alkyl$]_2$, $N[(C_3-C_8)$-cycloalkyl$]_2$, $NH-CO-(C_1-C_8)$-alkyl, NH—CO—($C_3$–$C_8$)-cycloalkyl; $SO_3H$, $SO_2$—$NH_2$, $SO_2$—NH—($C_1$–$C_8$)-alkyl, $SO_2$—NH—($C_3$–$C_8$)-cycloalkyl; NH—$SO_2$—$NH_2$; NH—$SO_2$—($C_1$–$C_8$)-alkyl, NH—$SO_2$—($C_3$–$C_8$)-cycloalkyl; O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$;

($C_1$–$C_8$)-alkyl, ($C_3$–$C_8$)-cycloalkyl, where in the alkyl groups in each case one to seven hydrogen atoms may be replaced by fluorine;

R6 is $(CH_2)_{0-6}$—R9, $(CH_2)_{0-6}$—COOH, $(CH_2)_{0-6}$—COO—($C_1$–$C_6$)-alkyl, $(CH_2)_{0-6}$—$CONH_2$, $(CH_2)_{0-6}$—CH(NHR15)-COR16, F, Cl, Br, CN, ($C_1$–$C_{18}$)-alkyl, ($C_3$–$C_4$)-cycloalkyl, ($C_6$–$C_8$)-cycloalkyl, where in the alkyl radicals or cycloalkyl radicals up to seven hydrogen atoms may be replaced by fluorine;

R15 is H, C(O)—($C_1$–$C_6$)-alkyl;

R16 is OH, O—($C_1$–$C_6$)-alkyl, $NH_2$,

R7 is $(CH_2)_{0-4}$—R12, H, ($C_1$–$C_{12}$)-alkyl, ($C_3$–$C_4$)-cycloalkyl, ($C_6$–$C_8$)-cycloalkyl, COO($C_1$–$C_6$)-alkyl, COO($C_3$–$C_8$)-cycloalkyl, where in the alkyl radicals or cycloalkyl radicals up to seven hydrogen atoms may be replaced by fluorine;

R8 is $(CH_2)_{0-4}$—R14, ($C_1$–$C_{12}$)-alkyl, ($C_3$–$C_4$)-cycloalkyl, ($C_6$–$C_8$)-cycloalkyl, where in the alkyl or cycloalkyl radicals up to seven hydrogen atoms may be replaced by fluorine atoms;

R9, R12, R14 independently of one another are phenyl, 1- or 2-naphthyl, biphenyl, or a heterocyclic radical, where the rings or ring systems are in each case substituted up to three times by F, Cl, Br, I, CN, OH, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, $S(O)_{0-2}$($C_1$–$C_8$)-alkyl, $S(O)_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_1$–$C_8$)-alkyl, NH—CO—($C_3$–$C_8$)-cycloalkyl, $SO_3H$; $SO_2$—$NH_2$, $SO_2$—NH—($C_1$–$C_8$)-alkyl, $SO_2$—NH—($C_3$–$C_8$)-cycloalkyl, NH—$SO_2$—$NH_2$; NH—$SO_2$—($C_1$–$C_8$)-alkyl, NH—$SO_2$—($C_3$–$C_8$)-cycloalkyl; O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$;

($C_1$–$C_8$)-alkyl, ($C_3$–$C_8$)-cycloalkyl, where in the alkyl groups in each case one to seven hydrogen atoms may be replaced by fluorine;

and their physiologically acceptable salts.

In a preferred embodiment, the invention provides compounds of the formula I in which R1, R2, R3, R4 independently of one another are H, F, Cl, Br, $N_3$, O($C_1$–$C_8$)-alkyl, ($C_1$–$C_8$)-alkyl and where in the alkyl groups one to seven hydrogen atoms may be replaced by fluorine;

where in each case at least one of the radicals R1, R2, R3 and R4 is different from hydrogen;

X is S, SO, $SO_2$;

Y is $(CH_2)_p$, where p may be 0, 1, 2 or 3;

R5 is ($C_1$–$C_{18}$)-alkyl, ($C_3$–$C_4$)-cycloalkyl, ($C_6$–$C_8$)-cycloalkyl, where in the alkyl groups up to seven hydrogen atoms may be replaced by fluorine;

$(CH_2)_{1-6}$—COOH, $(CH_2)_{1-6}$—COO—($C_1$–$C_6$)-alkyl, $(CH_2)_{1-6}$—$CONH_2$;

$CH_2$—CH(NHR10)-COR11, where R10 may be H or C(O)—($C_1$–$C_6$)-alkyl and R11 may be OH, O—($C_1$–$C_6$)-alkyl or $NH_2$;

phenyl, 1- or 2-naphthyl, biphenyl or a heterocyclic radical, where the rings or ring systems are in each case substituted up to three times by F, Cl, Br, I, CN, OH, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, $S(O)_{0-2}$($C_1$–$C_8$)-alkyl, $S(O)_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_1$–$C_8$)-alkyl, NH—CO—($C_3$–$C_8$)-cycloalkyl, $SO_3H$; $SO_2$—$NH_2$, $SO_2$—NH—($C_1$–$C_8$)-alkyl, $SO_2$—NH—($C_3$–$C_8$)-cycloalkyl, NH—$SO_2$—$NH_2$; NH—$SO_2$—($C_1$–$C_8$)-alkyl, NH—$SO_2$—($C_3$–$C_8$)-cycloalkyl; O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$;

($C_1$–$C_8$)-alkyl, ($C_3$–$C_8$)-cycloalkyl, where in the alkyl groups in each case one to seven hydrogen atoms may be replaced by fluorine;

R6 is $(CH_2)_{0-6}$—R9, $(CH_2)_{0-6}$—COOH, $(CH_2)_{0-6}$—COO—($C_1$–$C_6$)-alkyl, $(CH_2)_{0-6}$—$CONH_2$, $(CH_2)_{0-6}$—CH(NHR15)-COR16, F, Cl, Br, CN, ($C_1$–$C_{18}$)-alkyl, ($C_3$–$C_4$)-cycloalkyl, ($C_6$–$C_8$)-cycloalkyl, where in the alkyl radicals or cycloalkyl radicals up to seven hydrogen atoms may be replaced by fluorine;

R15 is H, C(O)—($C_1$–$C_6$)-alkyl;

R16 is OH, O—($C_1$–$C_6$)-alkyl, $NH_2$;

R7 is $(CH_2)_{0-4}$—R12, H, ($C_1$–$C_{12}$)-alkyl, ($C_3$–$C_4$)-cycloalkyl, ($C_6$–$C_8$)-cycloalkyl, COO($C_1$–$C_6$)-alkyl, COO($C_3$–$C_8$)-cycloalkyl, where in the alkyl radicals or cycloalkyl radicals up to seven hydrogen atoms may be replaced by fluorine;

R8 is $(CH_2)_{0-4}$—R14, ($C_1$–$C_{12}$)-alkyl, ($C_3$–$C_4$)-cycloalkyl, ($C_6$–$C_8$)-cycloalkyl, where in the alkyl or cycloalkyl radicals up to seven hydrogen atoms may be replaced by fluorine atoms;

R9, R12, R14 independently of one another are phenyl, 1- or 2-naphthyl, biphenyl, or a heterocyclic radical, where the rings or ring systems are in each case substituted up to three times by F, Cl, Br, I, CN, OH, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl. $S(O)_{0-2}$($C_1$–$C_8$)-alkyl, $S(O)_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_1$–$C_8$)-alkyl, NH—CO—($C_3$–$C_8$)-cycloalkyl, $SO_3H$; $SO_2$—$NH_2$, $SO_2$—NH—($C_1$–$C_8$)-alkyl, $SO_2$—NH—($C_3$–$C_8$)-cycloalkyl, NH—$SO_2$—$NH_2$; NH—$SO_2$—($C_1$–$C_8$)-alkyl, NH—$SO_2$—($C_3$–$C_8$)-cycloalkyl; O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$;

($C_1$–$C_8$)-alkyl, ($C_3$–$C_8$)-cycloalkyl, where in the alkyl groups in each case one to seven hydrogen atoms may be replaced by fluorine;

and their physiologically acceptable salts .

In another preferred embodiment, the invention provides compounds of the formula I in which R1, R2, R3, R4 independently of one another are H, F, Cl, Br, $N_3$, O($C_1$–$C_8$)-alkyl, ($C_1$–$C_8$)-alkyl and where in the alkyl groups one to seven hydrogen atoms may be replaced by fluorine;

where in each case at least one of the radicals R1, R2, R3 and R4 is different from hydrogen;

X is $SO_2$;

Y is $(CH_2)_p$, where p may be 0, 1 or 2;

R5 is $(C_1–C_8)$-alkyl, where in the alkyl group up to seven hydrogen atoms may be replaced by fluorine;

R6 is F, Cl, Br, CN, $(C_1–C_8)$-alkyl, where in the alkyl group up to seven hydrogen atoms may be replaced by fluorine;

R7 is H, $(C_1–C_{12})$-alkyl, where in the alkyl group up to seven hydrogen atoms may be replaced by fluorine;

R8 is $(C_1–C_{12})$-alkyl, where in the alkyl group up to seven hydrogen atoms may be replaced by fluorine;

and their physiologically acceptable salts.

The invention also contemplates compounds of the formula I in the form of their racemates, racemic mixtures and pure enantiomers, and also to their diastereomers and mixtures thereof.

The alkyl, alkenyl and alkynyl radicals in the substituents R1, R2, R3, R4, R5, R6, R7, R8, R9, R10, R11 and R12 can be straight-chain or branched.

Heterocycle or heterocyclic radical is to be understood as meaning ring systems which, in addition to carbon, also contain heteroatoms, such as, for example, nitrogen, oxygen or sulfur. This definition furthermore includes ring systems in which the heterocycle or heterocyclic radical is fused with benzene rings.

Preferred heterocycles or heterocyclic radicals are:

heteroaryls, such as benzimidazolyl,

1-[$(C_1–C_6)$-alkyl]benzimidazolyl, imidazolyl, 2- or 3-thienyl, 2- or 3-furyl, benzoxazolyl, benzothiazolyl, 2-, 3- or 4-pyridyl, pyrimidinyl, 4-, 5- or 6-pyridazin-2H-yl-3-one, 4-, 5- or 6-pyridazin-2-$(C_1–C_8)$-alkyl-2H-yl-3-one, 2-benzyl-4-, -5- or -6-pyridazin-2H-yl-3-one, 3- or 4-pyridazinyl, 2-, 3-, 4- or 8-quinolinyl, 1-, 3- or 4-isoquinolinyl, 1-phthalazinyl, 3- or 4-cinnolinyl, 2- or 4-quinazolinyl, 2-pyrazinyl, 2-quinoxalinyl, 2-, 4- or 5-oxazolyl, 3-, 4- or 5-isoxazolyl, 2-, 4- or 5-thiazolyl, 3-, 4- or 5-isothiazolyl, 1-[$(C_1–C_6)$-alkyl]-2-, -4- or -5-imidazolyl, 3-, 4- or 5-pyrazolyl, 1-[$(C_1–C_6)$-alkyl]-3-, -4- or -5-pyrazolyl, 1- or 4-[1,2,4]triazolyl, 4- or 5-[1,2,3]triazolyl, 1-[$(C_1–C_6)$-alkyl]-4- or -5-[1,2,3]triazolyl, 3-, 4- or 7-indolyl, N-[$(C_1–C_6)$-alkyl]-3-, -4- or -7-indolyl 2-[$(C,-C_6)$-alkyl]-3(2H)-indazolyl, 1-[$(C_1–C_6)$-alkyl]-3(1H )-indazolyl, 5-tetrazolyl, 1-[$(C_1–C_6)$-alkyl]-1H-tetrazolyl, 2-[$(C_1–C_6)$-alkyl]-2H-tetrazolyl.

Pharmaceutically acceptable salts are particularly suitable for medical applications, due to their greater solubility in water compared with the starting or base compounds. Said salts must have a pharmaceutically acceptable anion or cation. Suitable pharmaceutically acceptable acid addition salts of the compounds of the formula I are salts of inorganic acids such as hydrochloric acid, hydrobromic acid, phosphoric acid, metaphosphoric acid, nitric acid, sulfonic acid and sulfuric acid and also of organic acids such as, for example, acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid, tartaric acid and trifluoroacetic acid, furthermore L-ascorbic acid, salicylic acid, 1,2-benzisothiazol-3(2H)-one and 6-methyl-1,2,3-oxathiazin-4 (3H)-one 2,2-dioxide. For medicinal purposes, particular preference is given to using the chlorine salt. Suitable pharmaceutically acceptable basic salts are ammonium salts, alkali metal salts (such as sodium salts and potassium salts) and alkaline earth metal salts (such as magnesium salts and calcium salts).

Salts having a pharmaceutically unacceptable anion are likewise included within the scope of the present invention as useful intermediates for preparing or purifying pharmaceutically acceptable salts and/or for use in nontherapeutic applications, for example in-vitro applications.

The term "physiologically functional derivative" used herein relates to any physiologically acceptable derivative of an inventive compound, for example an ester which on administration to a mammal, for example humans, is capable of forming (directly or indirectly) such a compound or an active metabolite thereof.

A further aspect of this invention is the use of prodrugs of the compounds of the formula I. Such prodrugs may be metabolized in vivo to a compound of the formula I. These prodrugs may or may not be active themselves.

The physiologically functional derivatives furthermore include, for example, glucuronides, sulfuric acid esters, glycosides and ribosides.

The compounds of the formula I may also be present in various polymorphous forms, for example as amorphous and crystalline polymorphous forms. All polymorphous forms of the compounds of the formula I are included within the scope of the invention and are another aspect of the invention.

All references to "compound(s) according to formula (I)" refer hereinbelow to a compound/compounds of the formula (I) as described above and also to their salts, solvates and physiologically functional derivatives as described herein.

A "subject" may be a mammal, and is preferably a human.

The amount and effective amount of a compound according to formula (I) which is required in order to attain the desired biological effect depends on a number of factors, for example the specific compound selected, the intended use, the type of administration and the clinical state of the patient. In general, the daily dose is in the range from 0.3 mg to 100 mg (typically from 3 mg to 50 mg) per day per kilogram of body weight, for example 3–10 mg/kg/day. An intravenous dose can be, for example, in the range from 0.3 mg to 1.0 mg/kg and can be administered in a suitable manner as an infusion of 10 ng to 100 ng per kilogram per minute. Suitable infusion solutions for these purposes may contain, for example, from 0.1 ng to 10 mg, typically from 1 ng to 10 mg per milliliter. Individual doses may contain, for example, from 1 mg to 10 g of the active compound. Thus, ampules for injections can contain, for example, from 1 mg to 100 mg, and orally administerable individual dose formulations such as, for example, tablets or capsules can contain, for example, from 1.0 to 1000 mg, typically from 10 to 600 mg. In the case of pharmaceutically acceptable salts, the abovementioned masses relate to the mass of the benzothiazepine ion on which the salt is based. The compound used for the prophylaxis or therapy of the abovementioned conditions may be the compounds according to formula (I) themselves, but they are preferably present in the form of a pharmaceutical composition together with an acceptable carrier. The carrier must be naturally acceptable, in the sense that it is compatible with the other ingredients of said composition and is not harmful to the patient's health. The carrier may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The pharmaceutical compositions of the invention may be prepared according to any of the known pharmaceutical methods which essentially comprise mixing the ingredients with pharmacologically acceptable carriers and/or excipients.

Pharmaceutical compositions of the invention are those which are suitable for oral, rectal, topical, peroral (e.g. sublingual) and parenteral (e.g. subcutaneous, intramuscular, intradermal or intravenous) administration, although the most suitable manner of administration depends in each individual case on the nature and severity of the condition to be treated and on the nature of the compound according to formula (I) used in each case. Sugar-coated formulations and sugar-coated delayed-release formulations, too, are included within the scope of the invention. Preference is given to acid-resistant and enteric formulations. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be present in separate units as, for example, capsules, cachets, lozenges or tablets, which in each case contain a particular amount of the compound according to formula (I); as powders or granules; as solution or suspension in an aqueous or nonaqueous liquid; or as an oil-in-water or water-in-oil emulsion. As already mentioned, said compositions can be prepared according to any suitable pharmaceutical method which includes a step in which the active compound and the carrier (which may comprise one or more additional components) are contacted. In general, the compositions are prepared by uniform and homogeneous mixing of the active compound with a liquid and/or finely dispersed solid carrier, after which the product is shaped, if necessary. Thus a tablet, for example, may be prepared by pressing or shaping a powder or granules of the compound, where appropriate with one or more additional components. Pressed tablets can be prepared by tableting the compound in free-flowing form, for example a powder or granules, mixed, where appropriate, with a binder, lubricant, inert diluent and/or one or more surface active/dispersing agents in a suitable machine. Shaped tablets can be prepared by shaping the pulverulent compound, moistened with an inert liquid diluent, in a suitable machine.

Pharmaceutical compositions which are suitable for peroral (sublingual) administration include lozenges which contain a compound according to formula (I) with a flavoring, usually sucrose and gum arabic or tragacanth, and pastilles which comprise the compound in an inert base such as gelatin and glycerol or sucrose and gum arabic.

Suitable pharmaceutical compositions for parenteral administration preferably comprise sterile aqueous preparations of a compound according to formula (I) which are preferably isotonic with the blood of the intended recipient. These preparations are preferably administered intravenously, although they may also be administered subcutaneously, intramuscularly or intradermally as an injection. Said preparations may preferably be prepared by mixing the compound with water and rendering the obtained solution sterile and isotonic with the blood. Injectable compositions of the invention generally contain from 0.1 to 5% by weight of the active compound.

Suitable pharmaceutical compositions for rectal administration are preferably present as individual dose suppositories. These may be prepared by mixing a compound according to formula (I) with one or more conventional solid carriers, for example cocoa butter, and shaping the resulting mixture.

Suitable pharmaceutical compositions for topical application to the skin are preferably present as ointment, cream, lotion, paste, spray, aerosol or oil.

Carriers which may be used are petroleum jelly, lanolin, polyethylene glycols, alcohols and combinations of two or more of these substances. In general, the active compound is present at a concentration of from 0.1 to 15%, for example from 0.5 to 2%, by weight of the composition.

Transdermal administration is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from approx. 1% to 35%, preferably approx. 3% to 15%. A particular possibility is the release of the active compound by electrotransport or iontophoresis, as described, for example, in Pharmaceutical Research, 2(6): 318 (1986).

The invention furthermore provides a process for preparing the compounds of the formula I which comprises obtaining the compounds of the formula I by proceeding according to the reaction scheme below:

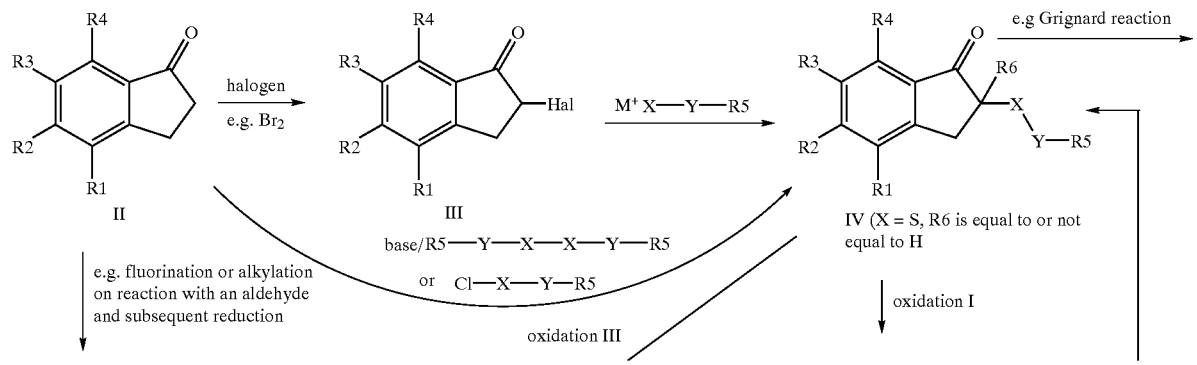
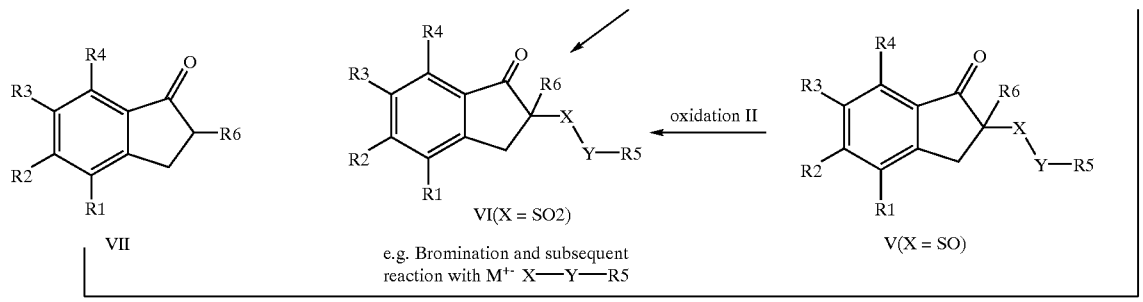
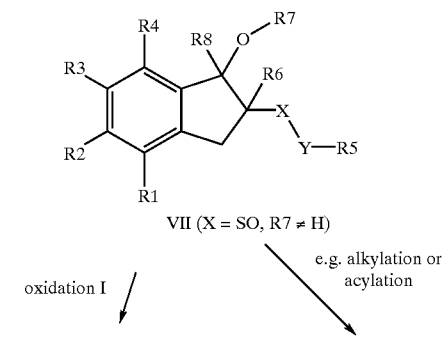
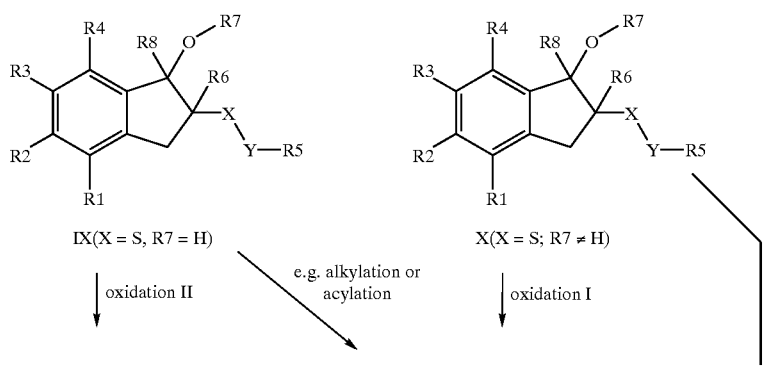

-continued

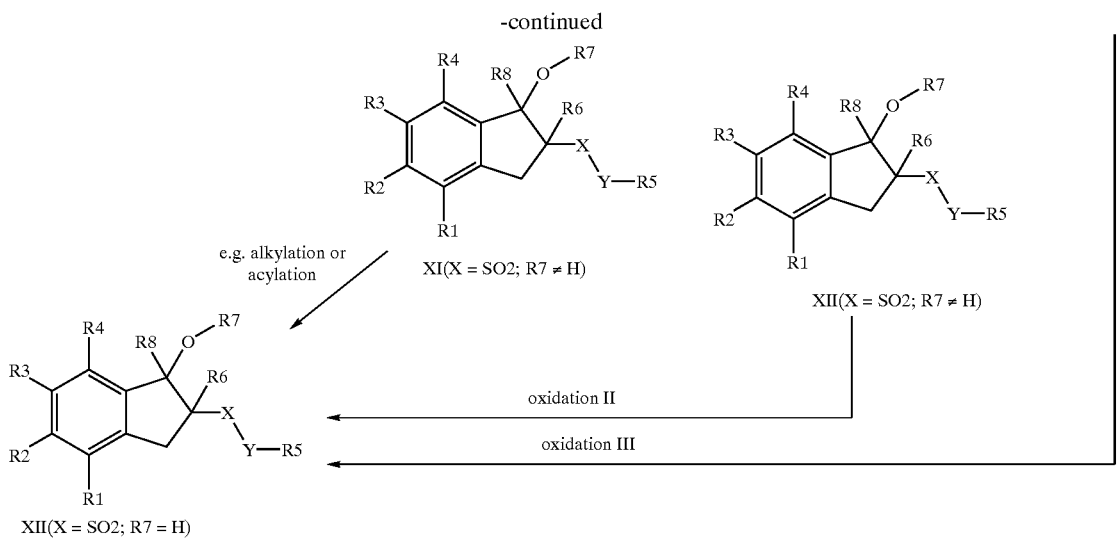

To this end, compounds of the formula II,

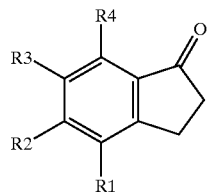

Formula II in which R1, R2, R3 and R4 are as defined above are converted with a halogen, such as, for example, bromine or chlorine, into a compound of the formula III.

The compounds of the formula III are converted further with metal salts of thiols of the formula H—X—Y—R5, where X is sulfur and Y and R5 are as defined above into compounds of the formula IV where X=S and R6=H. These metal salts can be employed as such or they can be generated in solution in situ from the thiol and a base, such as, for example, aqueous sodium hydroxide.

On the other hand, compounds of the formula IV where X=S and R6=H can be obtained by reacting compounds of the formula 11 with a base, such as, for example, lithium diisopropylamide, for example in tetrahydrofuran, and with a disulfide of the formula R5—Y—X—X—Y—R5 in which R5 and Y are as defined above and X=S; alternatively, instead of the disulfide, it is also possible to use a sulfenyl chloride of the formula Cl—X—Y—R5 where X=S and Y and R5 are as defined above (see, for example, D. Seebach et al.; Chem. Ber. 109, 1601–1616(1976)).

Compounds of the formula IV in which X=S and R6 is not hydrogen can be obtained, for example, as follows: compounds of the formula 11 are subjected, for example, to a fluorination, an alkylation or a condensation with an aldehyde and subsequent reduction, giving compounds of the formula VII which for their part can be converted, for example after bromination, with compounds of the formula M$^{+-}$X—Y—R5 where X=S and Y and R5 have the meanings described above into compounds of the formula IV where X=S and R6 is not hydrogen.

Compounds of the formula V in which X=SO and R6 is not hydrogen can be prepared, for example, by selective oxidation of the compound of the formula IV in which X=S, using one equivalent of peroxytrifluoroacetic acid (C. G. Venier et al.; J. Org. Chem. 47, 3773 (1982)). The preparation of the sulfoxides from the sulfides can also be carried out using manganese dioxide or chromic acid (D. Edwards et al.; J. Chem. Soc. 1954, 3272). Furthermore suitable for this oxidation is hydrogen peroxide in acetic anhydride (A. V. Sviridova et al.; J. Org. Chem (Russ), English Transl.; 7, 2577 (1971)).

Compounds of the formula VI in which X=SO$_2$ and R6 is not hydrogen can be obtained by oxidation using, for example, 2KHSO$_5$ xKHSO$_4$ xK$_2$SO$_4$ (Oxone), either from compounds of the formula IV in which X=S and R6 is not hydrogen or from compounds of the formula V in which X=SO and R6 is not hydrogen (see, for example, M. Hudlicky, Oxidations in Organic Chemistry, ACS Monograph 186, American Chemical Society, Washington, D.C., 1990).

Compounds of the formula VIII in which R8 is not hydrogen, R7 is hydrogen and X=S can be obtained, for example, by reacting compounds of the formula IV with a Grignard reagent. Stepwise oxidations and alkylation or acylation reactions give access to compounds of the formulae IX to XIII. Such compounds can also be obtained by employing compounds of the formula V or VI for the Grignard reaction.

Inorganic acids suitable for forming salts are, for example: hydrohalic acids, such as hydrochloric acid and hydrobromic acid, and also sulfuric acid, phosphoric acid and amidosulfonic acid.

Organic acids suitable for salt formation which may be mentioned are, for example: formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, 1,2-benzisothiazol-3(2H)-one, 6-methyl-1,2,3-oxathiazin-4 (3H)-one 2,2-dioxide.

The examples shown below serve to illustrate the invention without limiting it.

The melting points or decomposition points (m.p.) measured are uncorrected and generally depend on the heating rate.

TABLE 1

Examples

Formula I

| Example | R1 | R2 | R3 | R4 | X | Y | R5 | R6 | R7 | R8 | m.p. [° C.] |
|---------|----|----|----|----|----|----|----|----|----|----|-------------|
| 1 | H | Cl | H | H | $SO_2$ | — | $CH_3$ | F | H | $CH_3$ | 148 [MH$^+$] |
| 2 | H | Cl | H | H | $SO_2$ | — | $CH_3$ | F | H | $CF_3$ | 333.2 |

The compounds of the formula I are distinguished by beneficial actions on the metabolism of lipids, and they are particularly suitable for weight reduction and, after weight reduction, for maintaining a reduced weight in mammals and as anorectic agents. Accordingly, the instant compounds are particular useful for treating obesity by reducing weight, maintaining weight loss, and preventing obesity by, for example, preventing symptoms of weight loss.

The compounds are distinguished by their low toxicity and their few side effects. The compounds may be employed alone or in combination with other weight-reducing or anorectic active compounds. Further anorectic active compounds of this kind are mentioned, for example, in the Rote Liste, Chapter 01 (Arzneimittelverzeichnis für Deutschland, published by Rote Liste Service GmbH, Frankfurt) under weight-reducing agents/appetite suppressants, and may also include those active compounds which increase the energy turnover of the organism and thus lead to weight reduction or else those which influence the general metabolism of said organism such that increased calorie intake does not cause an enlargement of the fat depots and a normal calorie intake causes a reduction in the fat depots of said organism. The compounds are suitable for the prophylaxis and, in particular, for the treatment of problems of excess weight or obesity. The compounds are furthermore suitable for the prophylaxis and, in particular, for the treatment of type II diabetes, of arteriosclerosis and for the normalization of lipid metabolism and for the treatment of high blood pressure.

In a further aspect of the invention, the compounds of the formula I may be administered in combination with one or more further pharmacologically active substances which may be selected, for example, from the group consisting of antidiabetics, antiadipose agents, blood-pressure-lowering active compounds, lipid reducers and active compounds for the treatment and/or prevention of complications caused by diabetes or associated with diabetes.

Suitable antidiabetics include insulins, amylin, GLP-1 and GLP-2 derivatives such as, for example, those disclosed by Novo Nordisk A/S in WO 98/08871 and also oral hypoglycemic active compounds.

Said oral hypoglycemic active compounds preferably include sulfonyl ureas, biguanides, meglitinides, oxadiazolidinediones, thiazolidinediones, glucosidase inhibitors, glucagon receptor antagonists, GLP-1 agonists, potassium channel openers such as, for example, those disclosed by Novo Nordisk A/S in WO 97/26265 and WO 99/03861, insulin sensitizers, activators of insulin receptor kinase, inhibitors of liver enzymes involved in the stimulation of gluconeogenesis and/or glycogenolysis, for example glycogen phosphorylase inhibitors, modulators of glucose uptake and glucose elimination, lipid metabolism-modifying compounds such as antihyperlipidemic active compounds and antilipidemic active compounds, for example HMGCoA-reductase inhibitors, inhibitors of cholesterol transport/cholesterol uptake, inhibitors of the reabsorption of bile acid or inhibitors of microsomal triglyceride transfer protein (MTP), compounds which reduce food intake, PPAR and RXR agonists and active compounds which act on the ATP-dependent potassium channel of beta cells.

In one embodiment of the present invention, the present compounds are administered in combination with insulin.

In another embodiment, the compounds of the invention are administered in combination with a sulfonylurea such as, for example, tolbutamide, glibenclamide, glimepiride, glipizide, gliquidone, glisoxepide, glibornuride or gliclazide.

In another embodiment, the compounds of the present invention are administered in combination with a biguanide such as, for example, metformin.

In another embodiment, the compounds of the present invention are administered in combination with a meglitinide such as, for example, repaglinide.

In yet another embodiment, the compounds of the present invention are administered in combination with a thiazolidinedione such as, for example, troglitazone, ciglitazone, pioglitazone, rosiglitazone or the compounds disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione.

In yet another embodiment, the compounds of the present invention are administered in combination with a monoamine oxidase inhibitor such as disclosed, for example, in WO 01/12176. Particularly suitable for this purpose are [3(S),3a (S)]-3-methoxymethyl-7-[4,4,4-trifluorobutoxy]-3,3a,4,5-tetrahydro-1H-oxazolo[3,4-a]quinolin-1-one, (R)-5-(methoxymethyl)-3-[6-(4,4,4-trifluorobutoxy)benzofuran-3-yl]oxazolidin-2-one or (R)-5-(methoxymethyl)-3-[6-cyclopropylmethoxybenzofuran-3-yl]oxazolidin-2-one.

In another embodiment, the compounds of the present invention are administered in combination with an (x-glucosidase inhibitor such as, for example, miglitol or acarbose.

In yet another embodiment, the present compounds are administered in combination with an hCNTF (human ciliary neurotrophic factor) or derivatives thereof, such as, for example, CNTF$_{AX15}$ or modified CNTF$_{AX15}$, such as disclosed, for example, in Lambert et al., PNAS 98, 4652–4657.

In another embodiment, the compounds of the present invention are administered in combination with an active compound which acts on the ATP-dependent potassium channel of the beta cells, such as, for example, tolbutamide, glibenclamide, glimepiride, glipizide, gliclazide or repaglinide.

In yet another embodiment, the compounds of the present invention are administered in combination with an antihyperlipidemic active compound or an antilipidemic active compound such as, for example, cholestyramine, colestipol, clofibrate, gemfibrozil, lovastatin, pravastatin, simvastatin, atorvastatin, cerivastatin, fluvastatin, probucol, ezetimibe or dextrothyroxine.

In another embodiment, the compounds of the present invention are administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

Furthermore, the compounds of the invention may be administered in combination with one or more antiadipose agents or appetite-controlling active compounds.

Such active compounds may be selected from the group consisting of CART agonists, NPY antagonists, melanocortin 3 or 4 (MC3 or MC4) agonists, melanin-concentrating hormone (MCH) antagonists, orexin antagonists, H3 agonists, TNF agonists, CRF agonists, CRF BP antagonists, urocortin agonists, β3 adrenoceptor agonists, CCK agonists, serotonin re-uptake inhibitors, mixed serotonin and noradrenalin reuptake inhibitors, 5HT modulators, bombesin agonists, galanin antagonists, glucocorticoid receptor modulators, growth hormone, growth-hormone-releasing compounds, TRH agonists, uncoupling protein 2 or 3 modulators, leptin receptor agonists, leptin mimetics, dopamine agonists (bromocriptine, doprexin), lipase/amylase inhibitors, cannabinoid receptor 1 antagonists, modulators of acylation-stimulating protein (ASP), PPAR modulators, RXR modulators or TR-β agonists.

In one embodiment of the invention, the antiadipose agent is leptin or modified leptin.

In another embodiment, the antiadipose agent is dexamphetamine or amphetamine.

In another embodiment, the antiadipose agent is fenfluramine or dexfenfluramine.

In yet another embodiment, the antiadipose agent is sibutramine or the mono- and bis-demethylated active metabolite of sibutramine.

In another embodiment, the antiadipose agent is orlistate.

In another embodiment, the antiadipose agent is mazindol, diethylpropione or phentermine.

Furthermore, the compounds of the present invention may be administered in combination with one or more antihypertensive active compounds. Examples of antihypertensive active compounds are beta blockers such as alprenolol, atenol, timolol, pindolol, propanolol and metoprolol, ACE (angiotensin-converting enzyme) inhibitors such as, for example, benazepril, captopril, enalapril, fosinopril, lisinopril, quinapril and rampril, calcium channel blockers such as nifedipine, felodipine, nicardipine, isradipine, nimodipine, diltiazem and verapamil, and also alpha-blockers such as doxazosin, urapidil, prazosin and terazosin. Furthermore, reference may be made to Remington: The Science and Practice of Pharmacy, 19th edition, Gennaro, editor, Mack Publishing Co., Easton, Pa., 1995.

It is self-evident that every suitable combination of the compounds of the invention with one or more of the aforementioned compounds and optionally one or more other pharmacologically active substances is to be regarded as covered by the scope of protection of the present invention.

The following preparations serve to illustrate the invention, but without limiting it.

EXAMPLES

Example A

Soft gelatin capsules, comprising 100 mg of active compound per capsule:

|  | per capsule |
|---|---|
| Active compound | 100 mg |
| Triglyceride mixture fractionated from coconut butter | 400 mg |
| Capsule contents | 500 mg |

Example B

Emulsion, comprising 60 mg of active compound per 5 ml:

|  | per 100 ml of emulsion |
|---|---|
| Active compound | 1.2 g |
| Neutral oil | q.s. |
| Sodium carboxymethylcellulose | 0.6 g |
| Polyoxyethylene stearate | q.s. |
| Glycerol pure | 0.2 to 2.0 g |
| Flavoring | q.s. |
| Water (demineralized or distilled) | to 100 ml |

Example C

Rectal drug form, comprising 40 mg of active compound per suppository:

|  | per suppository |
|---|---|
| Active compound | 40 mg |
| Suppository base | ad 2 mg |

Example D

Tablets comprising 40 mg of active compound per tablet:

|  | per tablet |
|---|---|
| Lactose | 600 mg |
| Corn starch | 300 mg |
| Soluble starch | 20 mg |
| Magnesium stearate | 40 mg |
|  | 1000 mg |

Example E

Coated tablets comprising 50 mg of active compound per coated tablet:

|  | per coated tablet |
|---|---|
| Active compound | 50 mg |
| Corn starch | 100 mg |
| Lactose | 60 mg |
| Sec. calcium phosphate | 30 mg |
| Soluble starch | 5 mg |
| Magnesium stearate | 10 mg |
| Colloidal silica | 5 mg |
|  | 260 mg |

Example F

The following recipes are suitable for producing the contents of hard gelatin capsules:

| | | | |
|---|---|---|---|
| a) | Active compound | 100 mg | |
| | Corn starch | 300 mg | |
| | | 400 mg | |
| b) | Active compound | 140 mg | |
| | Lactose | 180 mg | |
| | Corn starch | 180 mg | |
| | | 500 mg | |

Example G

Drops can be prepared according to the following recipe (100 mg of active compound in 1 ml=20 drops):

| | |
|---|---|
| Active compound | 10 g |
| Methyl benzoate | 0.07 g |
| Ethyl benzoate | 0.03 g |
| Ethanol 96% | 5 ml |
| Demineralized water | ad 100 ml |

The activity of the compounds of formula I was assayed as follows:

Biological Test Model:

The anorectic action was tested on female NMRI mice. After removal of feed for 24 hours, the preparation to be tested was administered intraperitoneally (i.p.) or by gavage (po). The animals were housed singly and, with free access to drinking water, they were offered evaporated milk 30 minutes after administration of the preparation. The consumption of evaporated milk was determined and the general behavior of the animals was monitored every half an hour for 7 hours. The measured milk consumption was compared to that of vehicle-treated control animals.

Example 1

5-Chloro-2-fluoro-2-methanesulfonyl-1-methyl-indan-1-ol 1. 5-Chloro-2-methylsulfanylindan-1-one:

0.98 g (4 mmol) of 2-bromo-5-chloroindan-1-one and 0.42 g (6 mmol) of sodium thiomethoxide are suspended in 5 ml of ethanol, treated in an ultrasonic bath for 30 minutes and then stirred at room temperature for 90 minutes. The reaction mixture is concentrated under reduced pressure and chromatographed on silica gel using toluene/ethyl acetate 10/1. The eluates are concentrated under reduced pressure, giving 0.63 g of 5-chloro-2-methylsulfanylindan-1-one of melting point 90° C.

2. 5-Chloro-2-methanesulfonylindan-1-one 0.5 g (2.35 mmol) of 5-chloro-2-methylsulfanylindan-1-one is dissolved in 10 ml of methanol; at 0° C., a solution of 4.33 g (7.05 mmol) of $2KHSO_5 \times KHSO_4 \times K_2SO_4$ in 10 ml of water is added dropwise. The mixture is stirred at room temperature for 5 h; the methanol is distilled off and the aqueous residue is extracted with dichloromethane. The organic phase is separated off, dried over $MgSO_4$, filtered and concentrated under reduced pressure.

This gives 0.5 g of 5-chloro-2-methanesulfonylindan-1-one of melting point 197° C.

3. 5-Chloro-2-fluoro-2-methanesulfonylindan-1-one 0.734 g (3 mmol) of 5-chloro-2-methanesulfonylindan-1-one and 1.77 g (5 mmol) of N-fluoro-N'-(chloromethyl)triethylenediamine bis(tetrafluoroborate) are suspended in a mixture of 2.5 ml of water and 7.5 ml of acetonitrile and stirred under reflux for 4 h. The reaction mixture is cooled, concentrated under reduced pressure and purified chromatographically on silica gel using the mobile phase dichloromethane. This gives 5-chloro-2-fluoro-2-methanesulfonylindan-1-one of melting point 150° C.

4. 5-Chloro-2-fluoro-2-methanesulfonyl-1-methylindan-1-ol

At room temperature, 260 mg (1 mmol) of 5-chloro-2-fluoro-2-methanesulfonylindan-1-one are dissolved in 10 ml of dry tetrahydrofuran, and 0.33 ml of a 3M solution of methylmagnesium bromide in diethyl ether is added drop-

TABLE 2

Anorectic action, measured as a reduction in the cumulative milk consumption by treated animals compared with control animals

| Compound/Example Formula I | Dose [mg/kg] | Number of animals/cumulative milk consumption by treated animals N/[ml] | Number of animals/cumulative milk consumption by untreated control animals N/[ml] | Reduction in cumulative milk consumption as % of the control |
|---|---|---|---|---|
| Example 1 | 30 (i.p.) | 4/2.88 | 5/3.86 | 25 |

The table indicates that the compounds of the formula I exhibit good anorectic action.

The preparation of some examples is described in detail below; the other compounds of the formula I were obtained analogously:

wise with stirring. The reaction mixture is stirred at 50° C. for 3 h. A further 0.33 ml of the methylmagnesium bromide solution is then added, and the mixture is stirred at room temperature for another hour. After the reaction has ended, the reaction mixture is diluted with ethyl acetate and extracted successively with sat. ammonium chloride solution, sat. sodium bisulfite solution, sat. sodium bicarbonate solution and sat. sodium chloride solution. The organic phase is dried over magnesium sulfate, filtered and concentrated under reduced pressure. Chromatographic purification on silica gel (n-heptane/ethyl acetate 60/40) gives 5-chloro-2-fluoro-2-methanesulfonyl-1-methylindan-1-ol of melting point 148° C.

Example 2

5-Chloro-2-fluoro-2-methanesulfonyl-1-trifluoromethylindan-1-ol

When 5-chloro-2-fluoro-2-methanesulfonylindan-1-one is, instead of methylmagnesium bromide, reacted with trifluoromethyltrimethylsilane and tetrabutylammonium fluoride in tetrahydrofuran, 5-chloro-2-fluoro-2-methanesulfonyl-1-trifluoromethylindan-1-ol of molecular weight 332.7 ($C_{11}H_9ClF_4SO_3$); MS (ESI): 333.20 (MH$^+$) is obtained.

Additional advantages, features and modifications will readily occur to those skilled in the art. Therefore, the invention in its broader aspects is not limited to the specific details shown and described herein. Accordingly, various modifications may be made without departing from the spirit or scope of the general inventive concept as defined bye the appended claims and their equivalents.

As used herein and in the following claims, articles such as "the", "a" and "an" can connote the singular or plural.

All documents referred to herein are specifically incorporated herein by reference in their entireties.

The instant priority document, DE 10142659.3 filed Aug. 31, 2001 is incorporated herein by reference in its entirety.

What is claimed is:

1. A compound of the formula I:

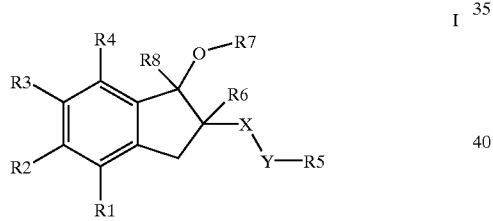

in which

R1, R2, R3, R4 independently of one another are H, F, Cl, Br, I, CN, $N_3$, $NO_2$, OH, $O(C_1-C_8)$-alkyl, $O(C_3-C_8)$-cycloalkyl, $O-CH_2$-phenyl, O-phenyl, $O-CO-(C_1-C_8)$-alkyl, $O-CO-(C_3-C_8)$-cycloalkyl, where in the alkyl radicals, up to seven hydrogen atoms may be replaced by fluorine;
$S(O)_{0-2}(C_1-C_8)$-alkyl, $S(O)_{0-2}(C_3-C_8)$-cycloalkyl, where in the alkyl radicals, up to seven hydrogen atoms may be replaced by fluorine;
$NH_2$, $NH-(C_1-C_8)$-alkyl, $NH-(C_3-C_8)$-cycloalkyl, $N[(C_1-C_8)$-alkyl$]_2$, $N[(C_3-C_8)$cycloalkyl$]_2$, $NH-CO-(C_1-C_8)$-alkyl, or $NH-CO-(C_3-C_8)$-cycloalkyl; $SO_3H$; $SO_2-NH_2$, $SO_2-NH-(C_1-C_8)$-alkyl, $SO_2-NH-(C_3-C_8)$-cycloalkyl; $SO_2-(C_1-C_6)$-alkyl $NH-SO_2-NH_2$; $NH-SO_2-(C_1-C_8)$-alkyl, $NH-SO_2-(C_3-C_8)$-cycloalky; $O-CH_2-COOH$, $O-CH_2-CO-O(C_1-C_8)$-alkyl, COOH, $COO(C_1-C_8)$-alkyl $CO-O-(C_3-C_8)$-cycloalkyl, $CO-NH_2$, $CO-NH(C_1-C_8)$-alkyl, $CO-N[(C_1-C_8)$-alkyl$]_2$;
$(C_1-C_8)$-alkyl, $(C_3-C_8)$cycloalkyl, $(C_2-C_8)$-alkenyl, or $(C_2-C_8)$-alkynyl, where in the alkyl, alkenyl and alkynyl groups, one to seven hydrogen atoms may be replaced by fluorine;
or one hydrogen may be replaced by OH, $OC(O)CH_3$, $O-CH_2-Ph$, $NH_2$, $NH-CO-OH_3$ or $N(COOCH_2Ph)_2$;
phenyl, 1- or 2-naphthyl,
where the aryl radicals may be substituted up to two times by
F, Cl, Br, CN,
OH, $(C_1-C_4)$-alkyl, $CF_3$, $O-(C_1-C_4)$-alkyl, $S(O)_{0-2}(C_1-C_6)$-alkyl, $NH_2$, $NH-SO_2-(C_1-C_4)$-alkyl, COOH, $CO-O-(C_1-C_4)$-alkyl, $CO-NH_2$ and where in the alkyl groups, one to seven hydrogen atoms may be replaced by fluorine;

X is $SO_2$;

Y is $(CH_2)_p$, where p may be 0,1, 2 or 3;

R5 is $(C_1-C_{18})$-alkyl, or $(C_3-C_8)$-cycloalkyl, where in the alkyl groups, up to seven hydrogen atoms may be replaced by fluorine;
$(CH_2)_{1-6}-COOH$, $(CH_2)_{1-6}-COO-(C_1-C_6)$-alkyl, $(CH_2)_{1-6}-CONH_2$;
$CH_2-CH(NHR10)-COR11$, where R10 may be H or $C(O)-(C_1-C_6)$-alkyl and R11 may be OH, $O-(C_1-C_6)$-alkyl or $NH_2$;
phenyl, 1- or 2-naphthyl, or biphenyl where the rings or ring systems are in each case substituted up to three times by
F, Cl, Br, I, CN, OH, $O(C_1-C_8)$-alkyl, $O(C_3-C_8)$-cycloalkyl, $O-CO-(C_1-C_8)$-alkyl, $O-CO-(C_3-C_8)$-cycloalkyl, $S(O)_{0-2}(C_1-C_8)$-alkyl, $S(O)_{0-2}(C_3-C_8)$-cycloalkyl; $NH_2$, $NH-(C_1-C_8)$-alkyl, $NH-(C_3-C_8)$-cycloalkyl, $N[(C_1-C_8)$-alkyl$]_2$, $N[(C_3-C_8)$-cycloalkyl$]_2$, $NH-CO-(C_1-C_8)$-alkyl, $NH-CO-(C_3-C_8)$-cycloalkyl, $SO_3H$; $SO_2-NH_2$, $SO_2-NH-(C_1-C_8)$-alkyl, $SO2\_NH-(C_3-C_8)$-cycloalkyl, $NH_1-SO_2-NH_2$; $NH-SO_2-(C_1-C_8)$-alkyl, $NH-SO_{2-(C3}-C_8)$-cycloalkyl; $O-CH_2-COOH$, $O-CH_2-CO-O(C_1-C_8)$-alkyl, COOH, $CO-O(C_1-C_8)$-alkyl, $CO-O-(C_3-C_8)$-cycloalkyl, $CO-NH_2$, $CO-NH(C_1-C_8)$-alkyl, $CO-N[(C_1-C_8)$-alkyl$]_2$;
$(C_1-C_8)$-alkyl, or $(C_3-C_8)$-cycloalkyl, where in the alkyl groups, in each case one to seven hydrogen atoms may be replaced by fluorine;

R6 is $(CH_2)_{0-6}-R9$, $(CH_2)_{0-6}-COOH$, $(CH_2)_{0-6}-COO-(C_1-C_6)$-alkyl, $(CH_2)_{0-6}-CONH_2$, $(CH_2)_{0-6}-CH(NHR15)-COR16$, F, Cl, Br, CN, $(C_1-C_{18})$-alkyl, $(C_3-C_4)$-cycloalkyl, or $(C_6-C_8)$-cycloalkyl, where in the alkyl radicals or cycloalkyl radicals, up to seven hydrogen atoms may be replaced by fluorine;

R15 is H, or $C(O)-(C_1-C_6)$-alkyl;

R16 is OH, $O-(C_1-C_6)$-alkyl, or $NH_2$,

R7 is $(CH_2)_{0-4}-R12$, H, $(C_1-C_{12})$-alkyl, $(C_3-C_4)$-cycloalkyl, $(C_6-C_8)$-cycloalkyl, $COO(C_1-C_6)$-alkyl, or $COO(C_3-C_8)$-cycloalkyl, where in the alkyl radicals or cycloalkyl radicals, up to seven hydrogen atoms may be replaced by fluorine;

R8 is $(CH_2)_{0-4}-R14$, $(C_1-C_{12})$-alkyl, $(C_3-C_4)$-cycloalkyl, or $(C_6-C_8)$-cycloalkyl, where in the alkyl or cycloalkyl radicals, up to seven hydrogen atoms may be replaced by fluorine atoms;

R9, R12, R14 independently of one another are
phenyl, 1- or 2-naphthyl, or biphenyl, where the rings or ring systems are in each case substituted up to three times by
F, Cl, Br, I, CN, OH, $O(C_1-C_8)$-alkyl, $O(C_3-C_8)$-cycloalkyl, $O-CO-(C_1-C_8)$-alkyl, $O-CO-(C_3-C_8)$-cycloalkyl, $S(O)_{0-2}(C_1-C_8)$-alkyl, $S(O)_{0-2}(C_3-C_8)$-cycloalkyl, $NH_2$, $NH-(C_1-C_8)$-alkyl, $NH-(C_3-C_8)$-cycloalkyl, $N[(C_1-C_8)$-alkyl$]_2$, $N[(C_3-C_8)$-cycloalkyl$]_2$, $NH-CO-(C_1-C_8)$-alkyl, NH—CO—($C_3$–$C_8$)-cycloalkyl, $SO_3H$; $SO_2$—$NH_2$, $SO_2$—NH—($C_1$–$C_8$)-alkyl, $SO_2$—NH—($C_3$–$C_8$)-cycloalkyl, NH—$SO_2$—$NH_2$; NH—$SO_2$—($C_1$–$C_8$)-alkyl, NH—$SO_2$—($C_3$–$C_8$)-cycloalkyl; O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$; ($C_1$–$C_8$)-alkyl, or ($C_3$–$C_8$)-cycloalkyl, where in the alkyl groups, in each case one to seven hydrogen atoms may be replaced by fluorine;

and their physiologically acceptable salts.

2. The compounds of the formula I, as claimed in claim 1, wherein

R1, R2, R3, R4 independently of one another are H, F, Cl, Br, $N_3$, O($C_1$–$C_8$)-alkyl, or ($C_1$–$C_8$)-alkyl and where in the alkyl groups, one to seven hydrogen atoms may be replaced by fluorine;

where in each case, at least one of the radicals R1, R2, R3 and R4 is different from hydrogen;

X is $SO_2$;

Y is $(CH_2)_p$, where p may be 0,1, 2 or 3;

R5 is ($C_1$–$C_{18}$)-alkyl, ($C_3$–$C_4$)-cycloalkyl, or ($C_6$–$C_8$)-cycloalkyl, where in the alkyl groups, up to seven hydrogen atoms may be replaced by fluorine;
$(CH_2)_{1-6}$—COOH, $(CH_2)_{1-6}$—COO—($C_1$–$C_{68}$)-alkyl, $(CH_2)_{1-6}$—$CONH_2$;
$CH_2$—CH(NHR10)—COR11, where R10 may be H or C(O)—($C_1$–$C_6$)-alkyl and R11 may be OH, O—($C_1$–$C_6$)-alkyl or $NH_2$;
phenyl, 1- or 2-naphthyl, or biphenyl where the rings or ring systems are in each case substituted up to three times by
F, Cl, Br, I, CN, OH, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, $S(O)_{0-2}$($C_1$–$C_8$)-alkyl, $S(O)_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_1$–$C_8$)-alkyl, NH—CO—($C_3$–$C_8$)-cycloalkyl, $SO_3H$; $SO_2$—$NH_2$, $SO_2$—NH—($C_1$–$C_8$)-alkyl, $SO_2$—NH—($C_3$–$C_8$)-cycloalkyl, NH—$SO_2$—$NH_2$; NH—$SO_2$—($C_1$–$C_8$)-alkyl, NH—$SO_2$—($C_3$–$C_8$)-cycloalkyl; O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_6$)-alkyl]$_2$; ($C_1$–$C_8$)-alkyl, or ($C_3$–$C_8$)-cycloalkyl, where in the alkyl groups, in each case one to seven hydrogen atoms may be replaced by fluorine;

R6 is $(CH_2)_{0-6}$—R9, $(CH_2)_{0-6}$—COOH, $(CH_2)_{0-6}$—COO—($C_1$–$C_6$)-alkyl, $(CH_2)_{0-6}$—$CONH_2$, $(CH_2)_{0-6}$—CH(NHR15)—COR16, F, Cl, Br, CN, ($C_1$–$C_{18}$)-alkyl, ($C_3$–$C_4$)-cycloalkyl, or ($C_6$–$C_8$)-cycloalkyl, where in the alkyl radicals or cycloalkyl radicals, up to seven hydrogen atoms may be replaced by fluorine;

R15 is H, or C(O)—($C_1$–$C_6$)-alkyl;

R16 is OH, O—($C_1$–$C_6$)-alkyl, or $NH_2$;

R7 is $(CH_2)_{0-4}$—R12, H, ($C_1$–$C_{12}$)-alkyl, ($C_3$–$C_4$)-cycloalkyl, ($C_6$–$C_8$)-cycloalkyl, COO($C_1$–$C_6$)-alkyl, or COO($C_3$–$C_8$)-cycloalkyl, where in the alkyl radicals or cycloalkyl radicals, up to seven hydrogen atoms may be replaced by fluorine;

R8 is $(CH_2)_{0-4}$—R14, ($C_1$–$C_{12}$)-alkyl, ($C_3$–$C_4$)-cycloalkyl, or ($C_6$–$C_8$)-cycloalkyl, where in the alkyl or cycloalkyl radicals, up to seven hydrogen atoms may be replaced by fluorine atoms;

R9, R12, R14 independently of one another are
phenyl, 1- or 2-naphthyl, or biphenyl where the rings or ring systems are in each case substituted up to three times by
F, Cl, Br, I, CN, OH, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, $S(O)_{0-2}$($C_1$–$C_8$)-alkyl, $S(O)_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_1$–$C_8$)-alkyl, NH—CO—($C_3$–$C_8$)-cycloalkyl; $SO_3H$; $SO_2$—$NH_2$, $SO_2$—NH—($C_1$–$C_8$)-alkyl, $SO_2$—NH—($C_3$–$C_8$)-cycloalkyl, $NH_1$—$SO_2$—$NH_2$; NH—$SO_2$—($C_1$–$C_8$)-alkyl, NH—$SO_{2—(C3}$–$C_8$)-cycloalkyl; O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$; ($C_1$–$C_8$)-alkyl, or ($C_3$–$C_8$)-cycloalkyl, where in the alkyl groups, in each case one to seven hydrogen atoms may be replaced by fluorine;

and their physiological acceptable salts.

3. the compounds of the formula I, as claimed in claim 1, wherein

R1, R2, R3, R4 independently of one another are H, F, Cl, Br, $N_3$, O($C_1$–$C_8$)-alkyl, or ($C_1$–$C_8$)-alkyl and where in the alkyl groups one to seven hydrogen atoms may be replaced by fluorine;

where in each case at least one of the radicals R1, R2, R3, R4 is different from hydrogen;

X is $SO_2$;

Y is $(CH_2)_p$, where p may be 0,1, or 2;

R5 is ($C_1$–$C_8$)-alkyl, where in the alkyl group up to seven hydrogen atoms may be replaced by fluorine;

R6 is F, Cl, Br, CN, or ($C_1$–$C_8$)-alkyl, where in the alklyl group up to seven hydrogen atoms may be replaced by fluorine;

R7 is H, or ($C_1$–$C_{12}$)-alkyl, where in the alkyl group up to seven hydrogen atoms may be replaced by fluorine;

R8 is ($C_1$–$C_{12}$)-alkyl, where in the alkyl group up to seven hydrogen atoms may be replaced by fluorine; and their physiological acceptable salts.

4. A pharmaceutical composition comprising an effective amount of a compound of formula I as claimed in claim 1, and a pharmaceutically acceptable carrier.

5. The pharmaceutical composition according to claim 4, further comprising one or more active compounds suitable for reducing weight or for the treatment of obesity.

6. The pharmaceutical composition according to claim 4, further comprising one or more of the agents selected from the group consisting of cathine, phenylpropanolamine, amfepramone, dexfenfluramine, sibutramine, orlistat, mazindol or phentermine or their salts for preparing a medicament for reducing weight in mammals.

7. A method for the treating obesity, comprising administering to a subject in need thereof, an effective amount of a compound according to formula I as claimed in claim 1.

8. A method of reducing weight in a mammal, comprising administering to said mammal an effective amount of a compound of formula I as claimed in claim 1.

9. A method of maintaining weight loss, comprising administering to a subject in need thereof, an effective amount of a compound of formula I as claimed in claim 1.

10. The method of claim 9, further comprising administering one or more active compounds for reducing weight in mammals.

* * * * *